US012599371B2

(12) United States Patent
Muller

(10) Patent No.: US 12,599,371 B2
(45) Date of Patent: Apr. 14, 2026

(54) APPARATUS AND SEPARATION CELL FOR SEPARATING DROPS OF BIOLOGICAL LIQUID FROM TRANSPORT AIR

(71) Applicant: NISO BIOMED S.R.L., Turin (IT)

(72) Inventor: Paul Muller, Marentino (IT)

(73) Assignee: NISO BIOMED S.R.L., Turin (IT)

( * ) Notice: Subject to any disclaimer, the term of this patent is extended or adjusted under 35 U.S.C. 154(b) by 421 days.

(21) Appl. No.: 18/547,296

(22) PCT Filed: Feb. 21, 2022

(86) PCT No.: PCT/IB2022/051513
§ 371 (c)(1),
(2) Date: Aug. 21, 2023

(87) PCT Pub. No.: WO2022/175909
PCT Pub. Date: Aug. 25, 2022

(65) Prior Publication Data
US 2024/0138820 A1 May 2, 2024

(30) Foreign Application Priority Data
Feb. 22, 2021 (IT) ........................ 102021000004034

(51) Int. Cl.
A61B 1/015 (2006.01)
A61B 1/273 (2006.01)
(Continued)

(52) U.S. Cl.
CPC .......... A61B 10/0045 (2013.01); A61B 1/015 (2013.01); A61B 1/273 (2013.01); A61B 2010/0061 (2013.01); A61M 1/71 (2021.05)

(58) Field of Classification Search
CPC ..... A61B 10/0045; A61B 1/015; A61B 1/273; A61B 2010/0061; A61M 1/71
See application file for complete search history.

(56) References Cited

U.S. PATENT DOCUMENTS 3,066,672 A * 12/1962 Crosby, Jr. ......... A61B 10/0045
600/573
10,646,108 B2 * 5/2020 Hassidov ............... A61B 1/126
(Continued)

FOREIGN PATENT DOCUMENTS

CN 109589144 A * 4/2019 ......... A61B 10/0045
EP 1596722 B1 12/2009
(Continued)

OTHER PUBLICATIONS

International Search Report for International Patent Application No. PCT/IB2022/051513, mailed May 30, 2022.

*Primary Examiner* — Guy K Townsend
(74) *Attorney, Agent, or Firm* — Armstrong Teasdale LLP

(57) ABSTRACT

An apparatus having a separation cell for separating drops of biological liquid from transport air in a flow coming from an endoscope is provided. The separation cell has an inner chamber having an upper inlet fluidically connectable to the endoscope, for receiving a flow containing drops of biological liquid mixed with transport air, a bottom outlet for exit of the drops of biological liquid, fluidically connectable to a suction pump and to an element for collecting and/or analyzing the drops of biological liquid, and an upper outlet for exit of the transport air and optionally of the drops of biological liquid and/or rinse water, fluidically connectable to a vacuum source. The separation cell forms a depression arranged between the upper inlet and the upper outlet. The depression extends downwards into the inner chamber and determines, for incoming transport air, a V-shaped path between the upper inlet and the upper outlet.

9 Claims, 2 Drawing Sheets

(51) Int. Cl.
    *A61B 10/00*        (2006.01)
    *A61M 1/00*        (2006.01)

(56)                 References Cited

U.S. PATENT DOCUMENTS

| | | | |
|---|---|---|---|
| 2008/0234563 A1* | 9/2008 | Regittnig | A61B 10/0045 |
| | | | 600/578 |
| 2014/0249448 A1* | 9/2014 | Furlong | A61B 1/00133 |
| | | | 600/563 |
| 2015/0018710 A1* | 1/2015 | Furlong | A61B 17/320016 |
| | | | 600/563 |
| 2015/0018711 A1* | 1/2015 | Furlong | A61B 1/31 |
| | | | 600/565 |
| 2015/0031951 A1* | 1/2015 | Furlong | A61B 1/00133 |
| | | | 600/106 |
| 2015/0032024 A1* | 1/2015 | Furlong | A61B 1/015 |
| | | | 600/566 |
| 2016/0166239 A1* | 6/2016 | Mikkaichi | A61B 1/015 |
| | | | 600/573 |
| 2017/0319188 A1* | 11/2017 | Furlong | A61B 1/31 |
| 2019/0254505 A1* | 8/2019 | Johnsen | A61M 39/22 |
| 2020/0015792 A1* | 1/2020 | Rezaie | A61M 1/71 |
| 2021/0076906 A1* | 3/2021 | Hassidov | A61B 1/0014 |
| 2021/0186469 A1* | 6/2021 | Johnsen | A61B 1/2676 |
| 2022/0338846 A1* | 10/2022 | Johnsen | A61B 10/0096 |
| 2024/0138820 A1* | 5/2024 | Muller | A61B 1/273 |

FOREIGN PATENT DOCUMENTS

| | | | | |
|---|---|---|---|---|
| WO | WO-2004075758 A1 * | 9/2004 | | A61B 10/04 |
| WO | WO-2018202265 A1 * | 11/2018 | | A61B 10/0096 |

\* cited by examiner

APPARATUS AND SEPARATION CELL FOR SEPARATING DROPS OF BIOLOGICAL LIQUID FROM TRANSPORT AIR

CROSS-REFERENCE TO RELATED APPLICATIONS

This application is a National Stage Application of International Patent Application No. PCT/IB2022/051513, having an International Filing Date of Feb. 21, 2022, which claims priority to Italian Application No. 102021000004034 filed Feb. 22, 2021, the entire contents of which are hereby incorporated by reference herein.

FIELD OF THE INVENTION

This invention relates to an apparatus and a separation cell for separating drops of biological liquid from transport air.

PRIOR ART

Endoscopy encompasses procedures and instruments for investigating and performing operations inside the human body, using methods which are aimed at reducing invasiveness as much as possible. The inside of the human body may be accessed by creating a suitable access route for the instrument; this is the case for thoracoscopy, laparoscopy or epiduroscopy (also known as surgical endoscopy), which use rigid endoscopes. Access may also be provided via orifices that are naturally present in the human body, for example via the mouth; in this case, flexible endoscopes are usually used which allow the operator to follow the access canal by bending the instrument and adapting it to the shape of the organ. This is the case for esophagogastroduodenoscopy, which is an instrumental diagnostic examination that allows the medical professional (doctor, nurse, etc.) to see and investigate inside the digestive system of a patient, in order to identify possible diseases affecting the esophagus, stomach and duodenum.

During esophagogastroduodenoscopy, the endoscope is introduced through the mouth of the patient and slowly pushed down along the various segments of the digestive system in order to inspect the esophagus, stomach and duodenum.

A further example is colonoscopy, which is a diagnostic examination aimed at examining the internal walls of the colon in order to discover possible lesions, ulcers, occlusions or tumors.

The endoscope is an optical instrument which consists of a (rigid or flexible) tube that is usually provided with cameras and light sources, the function of which is to observe cavities which are not normally visible, and internal access canals which allow biological fluids to be suctioned, the organ to be rinsed, instruments to be inserted for biopsy samples or procedures to be carried out.

The flexible endoscope is guided by the medical professional who handles the endoscope from the outside by means of mechanical tie rods. The tube is also connected to a light source which illuminates the inside of the body cavities to be examined.

In order to carry out the above analyses which require the use of the endoscope, for example esophagogastroduodenoscopy, the endoscope is usually connected, by means of a flexible tube (usually made of PVC), to a centralized system for generating a vacuum (i.e. a condition of negative pressure with respect to atmospheric pressure) inside a medical facility (of a hospital or ambulance) or at a portable vacuum pump. On account of this centralized system for generating a vacuum, the medical professional who handles the endoscope and carries out the analysis is able to suction the fluids present inside the cavities, for example drops of gastric acid, mucus, saliva, blood, interstitial fluids, digestive food residues and fecal particles, in order to clear the zone to be examined and be able to better see the internal walls and the mucous membranes of the cavity to be examined.

EP1596722B1 describes how this ability of the endoscope to suction drops of gastric acid from inside the explored cavities has been used to carry out a diagnostic analysis that, in real time during the esophagogastroduodenoscopy, makes it possible to identify the presence of indicators of infections and/or risk situations linked to gastroduodenal diseases.

The machine and the method described in EP1596722B1 include the steps of: suctioning a predetermined quantity of drops of gastric acid during an endoscopy, and conveying at least some of said suctioned drops to an analysis cell which, by carrying out an analysis of said drops of gastric acid, is able to obtain a diagnostic result regarding the presence of indicators of infections and/or risk situations linked to gastroduodenal diseases, in real time, before the end of the endoscopic examination.

However, the machine and the method described in EP1596722B1 suction the drops of gastric acid by means of a peristaltic pump inside the apparatus. The centralized system for generating a vacuum is in fact used, after the liquid is suctioned for analysis, solely to convey the excess drops of gastric acid to a discharge chamber and, after analysis, to suction the water used to rinse the components of the machine that have come into contact with the drops of gastric acid. During the initial step of suctioning the drops of gastric acid that are intended for analysis, the centralized system for generating a vacuum is in fact blocked by a solenoid valve. It is therefore the power of the peristaltic pump alone that draws the drops of gastric acid from the stomach to the analysis cell in which the drops of gastric acid are analyzed.

The machine and the method described in EP1596722B1 are therefore disadvantageous in that they have a long overall analysis time and are not very effective in collecting the quantity of drops of gastric acid required for analysis.

The use of a peristaltic pump as the only motive force for the drops of biological liquid in fact slows down the time taken for the drops to arrive at the analysis cell and thus increases the overall time of the medical examination. In order to be able to analyze the drops of biological liquid, it is also necessary for a certain quantity of drops to arrive at the analysis cell; if the time taken for the drops to arrive at the cell is long, the time required for the correct quantity of drops of biological liquid to be collected inside the cell in order to be able to carry out the analysis is even longer.

The lower suction power of the peristaltic pump not only makes suction slower, but also considerably reduces the quantity of drops of biological liquid transported to the analysis cell; as a result, a significant percentage of medical analyses in which it is necessary to draw and/or analyze drops of biological liquid are not completed by the medical professional due to an insufficient quantity of drops of biological liquid arriving at the means for collecting and/or analyzing said liquid.

There is therefore a need in the market for the possibility to provide an instrument that makes the collection and/or analysis of drops of biological liquid, which collection and/or analysis is carried out during a medical examination performed by means of endoscopy, for example in esophagogastroduodenoscopy, quick to carry out and that allows a larger quantity of drops of biological liquid to be suctioned from a greater number of patients.

SUMMARY OF THE INVENTION

The object of this invention is therefore that of providing an instrument that makes the collection and/or analysis of drops of biological liquid, which collection and/or analysis is carried out during a medical examination performed by means of endoscopy, for example in esophagogastroduodenoscopy, quick to carry out and that allows a larger quantity of drops of biological liquid to be suctioned from a greater number of patients.

This object is achieved, according to a first aspect of the present invention, by an apparatus, and, according to a second aspect of the present invention, by a cell as described and claimed herein. Preferred embodiments of the apparatus and the cell are also described.

This object is therefore achieved by an apparatus and by a separation cell for separating drops of biological liquid from transport air as outlined in the accompanying claims, the definitions of which form an integral part of this description.

BRIEF DESCRIPTION OF THE DRAWINGS

The invention will be better understood from the following detailed description of preferred embodiments thereof, given by way of non-limiting example and with reference to the accompanying figures, in which.

In the accompanying figures, identical or similar elements are denoted by the same reference signs.

DETAILED DESCRIPTION OF THE INVENTION

Figure 1:
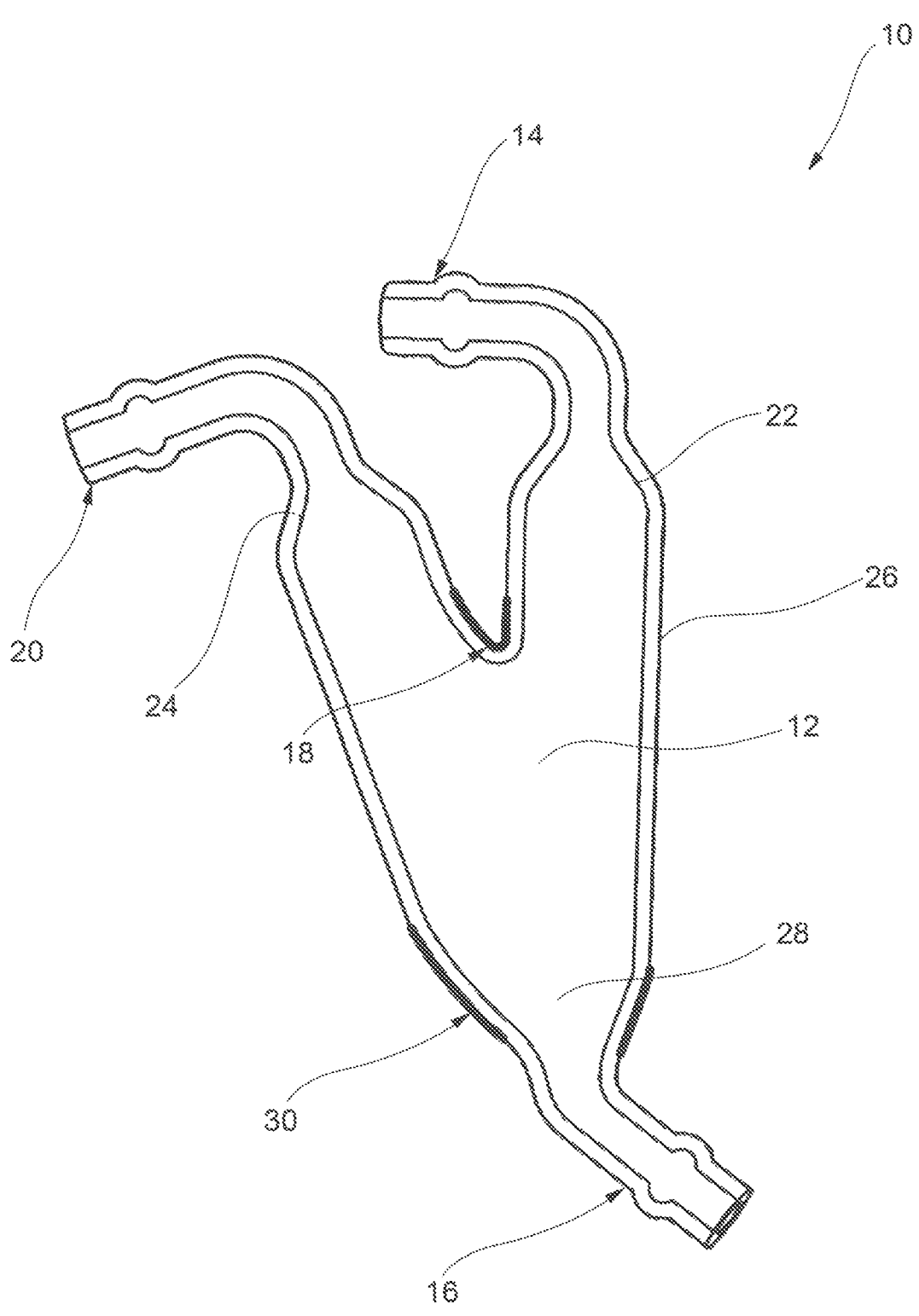
FIG. 1 shows the separation cell according to this invention.
Figure 2:
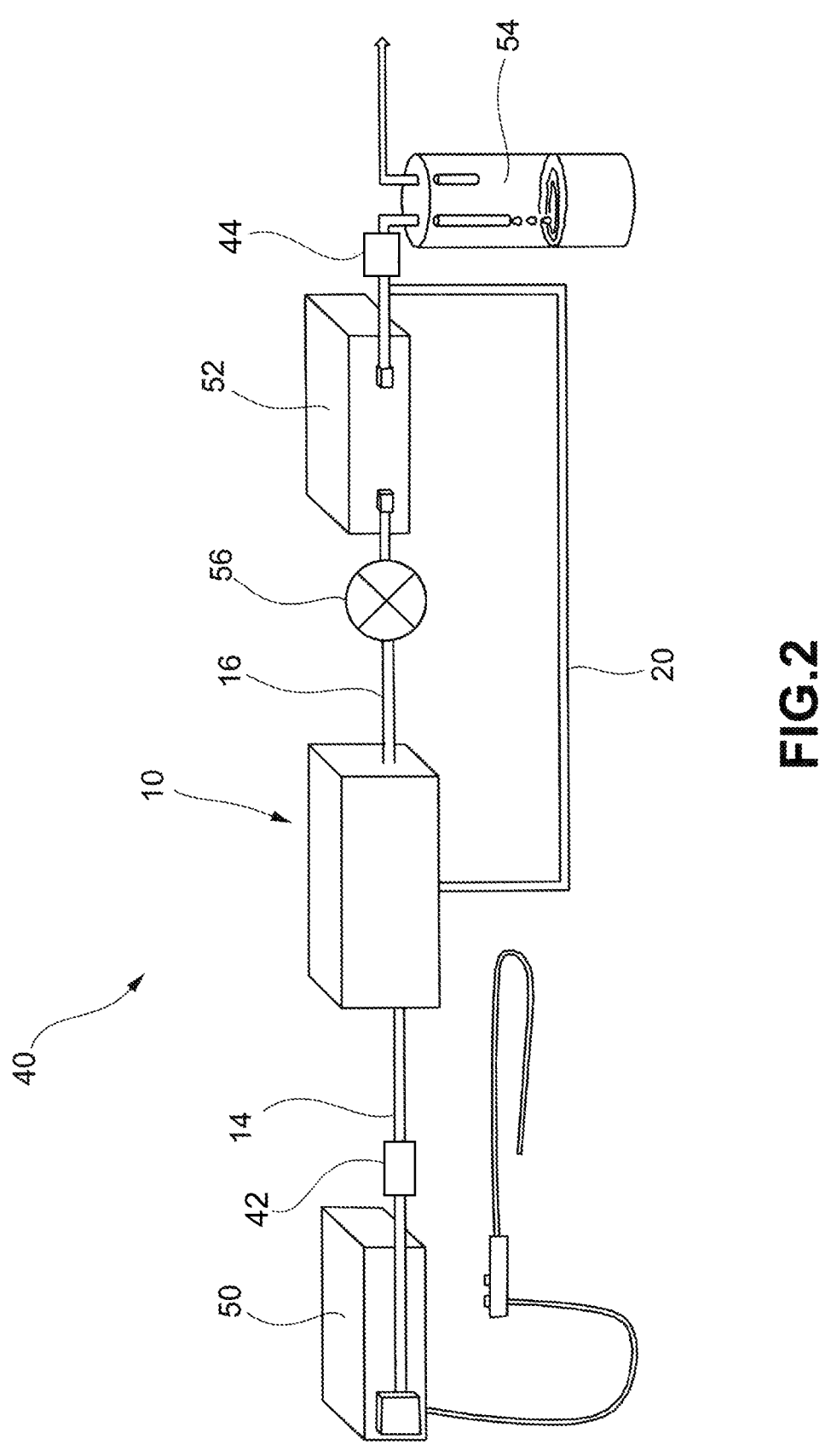
FIG. 2 is a simplified view of an apparatus comprising the separation cell according to this invention.

With reference to FIGS. 1 and 2, a first subject matter of this invention is shown, i.e. an apparatus 40 comprising:
a first connecting element 42 for an endoscope 50;
a second connecting element 44 for a vacuum source 54;
a suction pump 56;
a means for collecting and/or analyzing 52 the drops of biological liquid, functionally associated with the suction pump 56;
a separation cell 10 for separating drops of biological liquid from transport air in a flow coming from the endoscope 50, which separation cell comprises
an inner chamber 12 which has
an upper inlet 14 fluidically connectable to the endoscope 50, for receiving a flow containing drops of biological liquid mixed with transport air, a bottom outlet 16 for the exit of the drops of biological liquid, fluidically connectable to a suction pump 56 and thus to the means for collecting and/or analyzing 52 the drops of biological liquid,
an upper outlet 20 for the exit of the transport air, fluidically connectable to the vacuum source 54;
wherein the cell 10 forms a depression 18, arranged between the upper inlet 14 and the upper outlet 20, which depression extends downwards into the inner chamber 12 and determines, for the incoming transport air, a V-shaped path between the upper inlet 14 and the upper outlet 20;

wherein said separation cell 10 is arranged between and fluidically connected to the first connecting element 42 for the endoscope 50, the second connecting element 4) for the vacuum source 54, the suction pump 56, and the means for collecting and/or analyzing 52.

A further subject matter of this invention is a separation cell 10 for separating drops of biological liquid from transport air in a flow coming from an endoscope 50, which separation cell comprises an inner chamber 12 which has
an upper inlet 14 fluidically connectable to an endoscope 50, for receiving a flow containing drops of biological liquid mixed with transport air, a bottom outlet 16 for the exit of the drops of biological liquid, fluidically connectable to a suction pump 56 and thus to means for collecting and/or analyzing 52 the drops of biological liquid,
an upper outlet 20 for the exit of the transport air and optionally for the exit of drops of biological liquid and/or rinse water, fluidically connectable to a vacuum source 54;
wherein the cell 10 forms a depression 18, arranged between the upper inlet 14 and the upper outlet 20, which depression extends downwards into the inner chamber 12 and determines, for the incoming transport air, a V-shaped path between the upper inlet 14 and the upper outlet 20;
wherein the upper inlet 14 and the bottom outlet 16 are substantially aligned in a vertical direction and the cell 10 further forms a substantially vertical side wall 26 extending between the upper inlet 14 and the bottom outlet 16;
wherein the cell 10 forms a curved wall portion 30 which has a concavity facing the substantially vertical side wall 26.

According to a preferred embodiment, the endoscope 50 fluidically connectable to the upper inlet 14 is an endoscope for medical use, of the kind known to a person skilled in the art. It is preferably an endoscope for esophagogastroduodenoscopy, for colonoscopy or bronchoscopy, or for surgical endoscopy or laparoscopy.

According to a preferred embodiment, the drops of biological liquid are preferably drops of gastric acid.

According to an alternative embodiment of this invention, said drops of biological liquid may optionally be selected from: mucus, saliva, blood, interstitial fluids, or digestive food residues.

According to a preferred embodiment, the means for collecting and/or analyzing 52 the drops of biological liquid are preferably means that are known to a person skilled in the art and are, for example, containers for collecting liquids, automatic sampling systems, or analysis cells for measuring parameters (such as the pH) of the drops of biological liquid.

According to a preferred embodiment, the vacuum source is preferably a vacuum pump of the kind known to a person skilled in the art, or a centralized vacuum system for a medical facility (of a hospital, ambulance, etc.) that is also of the kind known to a person skilled in the art.

The cell 10 according to this invention preferably further comprises a portion 22 which widens, away from the upper inlet 14 and towards the depression 18, and preferably a portion 24 which narrows, away from the depression 18 and towards the upper outlet 20.

According to a preferred embodiment, the upper inlet 14 preferably forms a tubular portion which has a given diameter, while the widening portion 22 is preferably a conical intermediate connection portion arranged between the tubular portion of the upper inlet 14 and a cylindrical portion which has a greater diameter than the diameter of the tubular portion of the upper inlet 14 and ends at the depression 18.

Again according to a preferred embodiment, the upper outlet 20 preferably forms a tubular portion which has a given diameter, while the narrowing portion 24 is preferably a conical intermediate connection portion arranged between the tubular portion of the upper outlet 20 and a cylindrical portion which has a greater diameter than the diameter of the tubular portion of the upper outlet 20 and starts from the depression 18.

According to a preferred embodiment of the cell 10 according to this invention, the inner diameter of the tubular portion of the upper inlet 14 preferably has a ratio of 1:3 with respect to the inner diameter of the cylindrical portion which ends at the depression 18. This ratio advantageously makes it possible to create, in the cylindrical portion which ends at the depression 18, a zone where the flow coming from the endoscope 50 has a lower pressure than in the tubular portion of the upper inlet 14. This effect is known to a person skilled in the art as the "Venturi effect".

Again, according to a preferred embodiment of the cell 10 according to this invention, the inner diameter of the tubular portion of the upper outlet 20 preferably has a ratio of 1:3 with respect to the inner diameter of the cylindrical portion which starts from the depression 18.

This ratio advantageously makes it possible to create, in the cylindrical portion which starts from the depression 18, a zone where the transiting flow has a lower pressure than in the tubular portion of the upper outlet 20.

This effect is known to a person skilled in the art as the "Venturi effect".

As described above, the upper inlet 14 and the bottom outlet 16 according to this invention are substantially aligned in a vertical direction and the cell 10 further forms a substantially vertical side wall 26 extending between the upper inlet 14 and the bottom outlet 16. The feature whereby the upper inlet 14 and the bottom outlet 16 are substantially aligned in a vertical direction advantageously means that the drops of biological liquid arriving from the endoscope 50 are able, when entering by means of the upper inlet 14, to have the most linear and direct path possible towards the bottom outlet 16.

The shape of the depression 18 and of the cylindrical portion that ends at the depression 18 advantageously reduce the pressure of the flow coming from the endoscope 50 with respect to the pressure of the flow inside the tubular portion of the upper inlet 14.

According to a preferred embodiment, the upper inlet 14 preferably extends in a substantially horizontal direction.

Therefore, according to a preferred embodiment of the cell as described above, the flow coming from the endoscope 50, which flow comprises drops of biological liquid mixed with transport air, enters into the tubular portion of the upper inlet 14, which inlet, by preferably extending in a substantially horizontal direction and also being preferably and substantially aligned with the bottom outlet 16 in a vertical direction, thus generates a substantially L-shaped path for the flow; this causes the flow to impact against the substantially L-shaped part of the wall of the upper inlet 14.

Moreover, the feature of providing a widened diameter, and thus reduced pressure, in the widening portion 22 and in the subsequent cylindrical portion that ends at the depression 18, by comparison with the tubular portion of the upper inlet 14, advantageously makes it possible for the drops of biological liquid that preferably have a diameter substantially equal to that of the tubular portion of the upper inlet 14, when passing from the tubular portion of the upper inlet

14 to the widening portion 22 and the subsequent cylindrical portion that ends at the depression 18, as a result of the drop in pressure, to be able to more easily separate from the transport air, thus allowing the drops of biological liquid to fall, by gravity and inertia, towards the bottom outlet 16, and allowing the transport air to be suctioned towards the upper outlet 20 as a result of the force generated by the vacuum source.

Therefore, the aforesaid increase in diameter (with a subsequent reduction in pressure), the aforesaid impact and the feature of having a substantially vertical side wall 26 extending between the upper inlet 14 and the bottom outlet 16 allow initial separation of the transport air and the drops of biological liquid. In fact, these drops of biological liquid, by impacting against the substantially L-shaped part of the wall of the upper inlet 14 and entering the widening portion 22 and the subsequent cylindrical portion that ends at the depression 18, where the drops experience a decrease in pressure, may be more easily separated from the transport air and percolate by gravity and inertia along the substantially vertical side wall 26 until they reach the upper outlet 20. The transport air, however, following the V-shaped path set by the depression 18, is sucked towards the upper outlet 20 as a result of the force generated by the vacuum source. The decrease in pressure upon leaving the upper inlet 14 thus promotes the separation between the drops of biological liquid and the transport air: the ratio between the inner diameter of the tubular portion of the upper inlet 14 and the inner diameter of the cylindrical portion that ends at the depression 18 makes it possible for the pressure of the flow of drops of biological liquid plus transport air to decrease when passing between the tubular portion and the cylindrical portion, thus reducing the speed of motion of the flow and allowing the drops of biological liquid and transport air to separate. In this way, the suction force generated by the vacuum source does not influence the motion of the drops of biological liquid that percolate by gravity and inertia along the side wall 26, but only influences the motion of the transport air that flows, from the cylindrical portion that ends at the depression 18, reversing its direction of motion, following the V-shaped path set by the depression 18, inside the cylindrical portion that starts from the depression 18, in order to exit the cell 10 via the upper outlet 20.

These features allow the drops of biological liquid to percolate along the side wall 26 and thus reach the bottom outlet 16, through which the drops, separated from the transport air, are discharged from the cell 10.

Again, according to a preferred embodiment of the cell 10 according to this invention, the upper inlet 14 and the upper outlet 20 are preferably substantially pointed towards the same direction or according to respective directions that form an acute angle with each other. Said acute angle is preferably between 3° and 25°.

The cell 10 according to this invention also preferably forms a bottom portion 28 of the inner chamber 12, which bottom portion tapers towards the bottom outlet 16.

The bottom portion 28 preferably creates, for the drops of biological liquid percolating along the side wall 26, a path for connecting to the bottom outlet 16, where the drops of biological liquid may then be discharged from the cell 10.

The inner diameter of the bottom outlet 16 is preferably smaller than the inner diameter of the bottom portion 28. As a result of the Venturi effect (known to a person skilled in the art), this feature increases the pressure, and therefore speed, of the flow composed of the drops of biological liquid arriving at the bottom portion 28, when said drops run inside the bottom outlet 16.

As described above, the cell 10 further forms a curved wall portion 30 which has a concavity facing the substantially vertical side wall 26.

The curved wall portion 30 has a radius of curvature between 20 mm and 50 mm, and the distance between the curved wall portion 30 and the side wall 26 is preferably between 10 mm and 30 mm.

The feature of providing a curved wall portion 30 having a concavity facing the side wall 26 is advantageous during the step of rinsing the cell. After the cell 10 has been used, it is preferably advisable to rinse the cell 10. This rinsing may be carried out by making the water, which is optionally mixed with one or more surfactants, flow from the upper inlet 14 and flow out from the upper outlet 20. The feature of providing a curved wall portion 30 having a concavity facing the side wall 26 advantageously means that the rinse water rinses the bottom portion 28 of the cell in order to then flow out of the upper outlet 20. In fact, the rinse water flowing from the upper inlet 14 primarily descends towards the bottom portion 28 but, as a result of impacting against the curved wall portion 30, generates a centripetal vortex motion with respect to a central portion of the inner chamber 12 in order to then flow out of the upper outlet 20. This prevents any liquids that have not been drained by the rinse water from stagnating. This vortex is advantageously created during the rinse step and not during the use of the cell 10 for separating the drops of biological liquid from the transport air, since the quantity of drops of biological liquid flowing inside the cell 10 is considerably less than the quantity of rinse water used during the rinse step. In fact, the quantity of drops of biological liquid flowing inside the cell 10 is preferably less by an order of approximately 400 times than the quantity of rinse water used during the rinse step. The shape of the cell 10, in particular the curved wall portion 30, in fact advantageously makes it possible to create a vortex flow only when the flow that runs therein from the upper inlet 14 is in such a quantity as to impact against the curved wall portion 30, thus generating a vortex in a central portion of the inner chamber 12.

According to a preferred embodiment of the cell 10 according to this invention, the cell 10 is preferably made of glass or chemically inert and rigid materials, and preferably has a thickness so as to support a negative pressure of between −500 mmHg and −600 mmHg. Said thickness is even more preferably between 1.5 mm and 3 mm.

With reference to that described above and in particular to the first subject matter of this invention, namely the apparatus 40, the first and the second connecting elements 42 and 44 are preferably a tube or a connector or a valve. Furthermore, the vacuum source 54 of the apparatus 40 is preferably a centralized vacuum system of a hospital facility and the suction pump 56 is preferably a peristaltic pump.

The apparatus 40 according to this invention preferably comprises:

a first connecting element 42 for an endoscope 50;
a second connecting element 44 for a vacuum source 54;
an endoscope 50;
a vacuum source 54;
a suction pump 56;
a means for collecting and/or analyzing 52 the drops of biological liquid, functionally associated with the suction pump 56;
a separation cell 10 for separating drops of biological liquid from transport air in a flow coming from the endoscope 50, which separation cell comprises
an inner chamber 12 which has an upper inlet 14 fluidically connectable to the endoscope 50, for receiving a flow containing drops of biological liquid mixed with transport air, a bottom outlet 16 for the exit of the drops of biological liquid, fluidically connectable to a suction pump 56 and thus to the means for collecting and/or analyzing 52 the drops of biological liquid, an upper outlet 20 for the exit of the transport air and optionally for the exit of drops of biological liquid and/or rinse water, fluidically connectable to the vacuum source 54;

wherein the cell 10 forms a depression 18, arranged between the upper inlet 14 and the upper outlet 20, which depression extends downwards into the inner chamber 12 and determines, for the incoming transport air, a V-shaped path between the upper inlet 14 and the upper outlet 20;

wherein said separation cell 10 is arranged between and fluidically connected to the first connecting element 42 for the endoscope 50 and thus the endoscope 50, the second connecting element 44 for the vacuum source 54 and thus the vacuum source 54, the suction pump 56, and the means for collecting and/or analyzing 52.

According to a preferred embodiment of the apparatus 40 according to this invention, the drops of biological liquid are preferably drawn from the body cavities of a subject, for example from the stomach of a patient, by means of the endoscope 50. These drops of biological liquid, mixed with transport air, are preferably transported from the endoscope 50 into the cell 10, by passing through the upper inlet 14. Inside the cell 10, as described above, the drops of biological liquid are separated from the transport air. The transport air, passing through the upper outlet 20, is sucked out of the cell 10 as a result of the force generated by the vacuum source 54. Meanwhile, the drops of biological liquid, passing through the bottom outlet 16, are preferably pushed towards the means for collecting and/or analyzing 52 by a peristaltic pump 56 positioned between the bottom outlet 16 and the means for collecting and/or analyzing 52 the drops of biological liquid.

The separation cell 10 for separating drops of biological liquid from transport air and the apparatus 40 comprising said cell 10, according to this invention, therefore have the advantage of ensuring that the drops of biological liquid are effectively separated from the transport air. This separation is ensured by the shape of the cell according to this invention and by the combination of the motive force generated by a vacuum source and the motive force generated by a suction pump (for example a peristaltic pump). In so doing, the time needed to collect a suitable quantity of drops of biological liquid for the analysis of said drops is considerably reduced by comparison with known solutions.

As a result, the collection times are significantly optimized, and the minimum level of drops of biological liquid used to carry out the analysis is quickly reached. The examination (for example the esophagogastroduodenoscopy) is therefore fast, and a greater quantity of drops of biological liquid are collected.

Moreover, the feature of providing the apparatus 40 according to this invention comprising the separation cell 10 fluidically connectable to a suction pump 56 advantageously makes it possible, automatically, while thus preventing the need for manual intervention by an operator, for different steps to alternate: a separation step for separating the drops of biological liquid from the transport air in a flow coming from an endoscope 50, with the drops of biological liquid subsequently being conveyed to the means for collecting and/or analyzing 52, and a step of rinsing the cell 10. The apparatus 40 according to this invention therefore advantageously eliminates the need for any manual intervention by an operator in order to transition from the collection and analysis step to the rinse step.

According to a preferred embodiment of the apparatus 40 according to this invention, said suction pump 56, said means for collecting and/or analyzing 52 the drops of biological liquid and said separation cell 10 are preferably contained in the machine described in EP1596722B1 or in an automatic sampling system.

The cell and the apparatus according to this invention thus make the collection and/or analysis of drops of biological liquid, which collection and/or analysis is carried out during a medical examination performed by means of endoscopy, for example in esophagogastroduodenoscopy, quick to carry out, and allow a larger quantity of drops of biological liquid to be suctioned from a greater number of patients.

The invention claimed is:

1. An apparatus comprising:
a first connecting element for an endoscope;
a second connecting element for a vacuum source;
a suction pump;
a means for collecting and/or analyzing drops of biological liquid, functionally associated with the suction pump;
a separation cell for separating the drops of biological liquid from transport air in a flow coming from the endoscope, the separation cell comprising
an inner chamber that comprises
an upper inlet fluidically connectable to the endoscope, for receiving a flow containing the drops of biological liquid mixed with the transport air,
a bottom outlet for exit of the drops of biological liquid, fluidically connected to the suction pump and thus to the means for collecting and/or analyzing the drops of biological liquid,
an upper outlet for exit of the transport air and for exit of the drops of biological liquid and/or rinse water, fluidically connectable to the vacuum source;
wherein the separation cell forms a depression arranged between the upper inlet and the upper outlet, the depression extending downwards into the inner chamber and determining, for incoming transport air, a V-shaped path between the upper inlet and the upper outlet; and
wherein said separation cell is arranged between and fluidically connected to the first connecting element for the endoscope and thus the endoscope, the second connecting element for the vacuum source, the suction pump, and the means for collecting and/or analyzing the drops of biological liquid.

2. The apparatus of claim 1, wherein the vacuum source is a centralized vacuum system of a hospital facility and the suction pump is a peristaltic pump.

3. The apparatus of claim 1, comprising:
a first connecting element for an endoscope;
a second connecting element for a vacuum source;
an endoscope;
a vacuum source;
a suction pump;
a means for collecting and/or analyzing drops of biological liquid, functionally associated with the suction pump;
a separation cell for separating the drops of biological liquid from transport air in a flow coming from the endoscope, the separation cell comprising
an inner chamber that comprises
an upper inlet fluidically connectable to the endoscope, for receiving a flow containing the drops of biological liquid mixed with the transport air,
a bottom outlet for exit of the drops of biological liquid, fluidically connectable to the suction pump and thus to the means for collecting and/or analyzing the drops of biological liquid,
an upper outlet for exit of the transport air and for exit of the drops of biological liquid and/or rinse water, fluidically connectable to the vacuum source;
wherein the separation cell forms a depression arranged between the upper inlet and the upper outlet, the depression extending downwards into the inner chamber and determining, for incoming transport air, a V-shaped path between the upper inlet and the upper outlet; and
wherein said separation cell is arranged between and fluidically connected to the first connecting element for the endoscope and thus the endoscope, the second connecting element for the vacuum source and thus the vacuum source, the suction pump, and the means for collecting and/or analyzing the drops of biological liquid.

4. The apparatus of claim 1, wherein the upper inlet and the bottom outlet are substantially aligned in a vertical direction and the separation cell further forms a substantially vertical side wall extending between the upper inlet and the bottom outlet,
wherein the separation cell forms a curved wall portion having a concavity facing the substantially vertical side wall;
wherein the separation cell forms a bottom portion of the inner chamber, the bottom portion tapering towards the bottom outlet; and
wherein the curved wall portion having the concavity facing the substantially vertical side wall causes the rinse water to rinse the bottom portion of the separation cell and then flow out of the upper outlet.

5. The apparatus of claim 4, wherein the curved wall portion has a radius of curvature between 20 mm and 50 mm.

6. The apparatus of claim 4, wherein the separation cell further comprises a portion which widens, away from the upper inlet, towards the depression.

7. The apparatus of claim 4, wherein the separation cell further comprises a portion which narrows, away from the depression, towards the upper outlet.

8. The apparatus of claim 4, wherein the upper inlet extends in a substantially horizontal direction.

9. The apparatus of claim 4, wherein the upper inlet and the upper outlet are substantially pointed towards a same direction or according to respective directions that form an acute angle with each other.

* * * * *